(12) United States Patent
Al-Harthi (10) Patent No.: US 9,688,836 B2
(45) Date of Patent: Jun. 27, 2017

(54) HIGH-DENSITY POLYETHYLENE PREPARATION METHODS

(71) Applicant: KING FAHD UNIVERSITY OF PETROLEUM AND MINERALS, Dhahran (SA)

(72) Inventor: Mamdouh Ahmed Al-Harthi, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 171 days.

(21) Appl. No.: 14/796,885

(22) Filed: Jul. 10, 2015

(65) Prior Publication Data

US 2017/0009049 A1   Jan. 12, 2017

(51) Int. Cl.
| | | |
|---|---|---|
| C08G 61/10 | (2006.01) | |
| C08K 3/22 | (2006.01) | |
| C08F 210/02 | (2006.01) | |
| C08K 3/24 | (2006.01) | |
| C08K 9/02 | (2006.01) | |
| C08K 3/08 | (2006.01) | |
| C08F 2/44 | (2006.01) | |

(52) U.S. Cl.
CPC .............. *C08K 3/22* (2013.01); *C08F 210/02* (2013.01); *C08K 3/24* (2013.01); *C08F 2/44* (2013.01); *C08K 3/08* (2013.01); *C08K 9/02* (2013.01); *C08K 2201/011* (2013.01)

(58) Field of Classification Search
CPC ......... C08F 2108/02; C08K 9/02; C08K 3/16; C08K 2003/0812; C08K 2003/0818; C08K 2003/2206; C08K 2006/2244
USPC ................................................. 524/783, 785
See application file for complete search history.

(56) References Cited

U.S. PATENT DOCUMENTS

| | | |
|---|---|---|
| 6,312,828 B1 | 11/2001 | Akao |
| 8,163,347 B2 | 4/2012 | Marks et al. |
| 2008/0194736 A1 | 8/2008 | Lu |
| 2013/0317170 A1* | 11/2013 | Marks .................... B82Y 30/00 524/783 |

FOREIGN PATENT DOCUMENTS

KR    10-2012-0052904    5/2012

OTHER PUBLICATIONS

Yao Huang, et al., "Terpolymerization of Ethylene/Propylene/5-Ethylidene-2-Norbornene Using RAC-ET(IND)2ZRCL2 and Modified—Methylaluminoxane Metallocene Catalyst System," Journal of Polymer Materials, Apr.-Jun. 2013, vol. 30, Issue 2, Abstract Only.

Shokoufeh Hakim, et al., "Polyethylene Nanocomposite Prepared by a Metallocene Catalyst Supported on MMT Using a New Pretreatment Method," Journal of Polymer Research, May 2013, vol. 20, Issue 5, Abstract Only.

* cited by examiner

*Primary Examiner* — Jane L Stanley
(74) *Attorney, Agent, or Firm* — Oblon, McClelland, Maier & Neustadt, L.L.P.

(57) ABSTRACT

Methods of preparing high-density polyethylene (HDPE) nanocomposites by in situ polymerization with a zirconocene catalyst, a methylaluminoxane cocatalyst, a calcium zirconate nanofiller in a solvent. The calcium zirconate nanofiller, which is dispersed across the polyethylene matrix, is found to enhance catalyst activity, and other properties of the HDPE nanocomposites produced, including but not limited to flame retardency, crystallinity and surface morphology.

20 Claims, 7 Drawing Sheets

HIGH-DENSITY POLYETHYLENE PREPARATION METHODS

BACKGROUND OF THE INVENTION

Technical Field

The present invention relates to polymer production. More particularly, the present invention relates to methods for producing high-density polyethylene (HDPE) nanocomposites.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

The commercial success of polyethylene (PE) made it attractive for academic and industrial researchers to develop and improve its properties by proposing several techniques such as making new polyethylene-based composite. The selection of proper filler is very important to target the end usage [Zhang R X, Ni Q Q, Natsuki T, Iwamoto M (2007) Compos Strict 79: 90-96—incorporated herein by reference in its entirety]. The physiochemical characteristics of both the filler and the host polymer strongly control the final performance of the nanocomposites [Serkan T H, Dilek K (2007) J Reinforced Plastics and Composites 26: 113-121; Chow T S (1980) J Mate Sci 15:1873-1888—each incorporated herein by reference in its entirety]. In addition, the preparation method plays a significant role in shaping the final properties of the filled polymer. The small size of nano materials attracts researchers to use them as a replacement for the conventional fillers in the polymeric industry [Farzana H, Mehdi H, Masami O, Russel E, Gorga, (2006) Review article: Polymer-matrix Nanocomposites, Processing, Manufacturing, and Application: An Overview J Composite Materials September 1-65—incorporated herein by reference in its entirety]. The addition of those fillers during the polymerization as a drop in filler can affect the reaction mechanism and it can lead to higher active reaction [Mamdouh A H, Omar Y B, De S K, Reyad S (2013) U.S. Pat. No. 8,604,115; Mamdouh A H, Orner Y B, De S K, Reyad S (2013) U.S. Pat. No. 8,541,520; Hu Z, Liu C (2013) J Polym Res 20:39—each incorporated herein by reference in its entirety]. Different inorganic nanoparticles, such as titanium dioxide ($TiO_2$), silicon dioxide ($SiO_2$), aluminum trioxide ($Al_2O_3$) and zinc dioxide ($ZrO_2$) have been used to improve and enhance the polymer properties [(René J N, Walter R C, Paul S (2003) Macromol Mater Eng 288:44-49; Wang Z, Li G, Xie G, Zhang Z (2005) Macrom Chem and Phys 206: 258-262; Xu D C, Zhi W, Zheng F L, Yu L M, Ming Q Z (2007) Polym Test 26: 202-208; Owpradit W, Jongsomjit B (2008) Mate Chem and Phys 112:954-961; Jongsomjit B, Chaichana E, Praserthdam P (2005) J Matr Sci 40: 2043-2045; Kontou E, Niaounakis M (2006) Polymer 47:1267-1280; Chaichana E, Jongsomjit B. Praserthdam P (2007) Chem Eng Sci 62: 899-905; Li K T, Dai C L, Kuo C W (2007) Catalysis Communications 81209; Kuoab M C, Tsaia C M, Huanga J C, Chena M (2005) Mate Chem and Phy 90:185-195; Desharun C, Jongsomjit B, Praserthdam P (2008) Cata Comm 9:522-528; Jongsomjit B. Panpranot J, Okada M, Shiono T, Praserthdam P (2006) Iranian. Polymer Journal (English Edition) 15:433-439; Jongsomjit B, Panpranot J, Praserthdam P (2007) Mat Let 61:1376-1379— each incorporated herein by reference in its entirety]. Moreover, these inorganic nanofillers can shape the morphology of the polymer during the reaction to produce bigger particles [Abdul Kaleel S H, Bahuleyan B K, De S K, Khan M J, Sougrat R, Al-Harthi M A (2012) J Ind and Eng Chem 18: 1836-1840; Bahuleyan B K, Atieh M A, De S K, Khan M J, Al-Harthi M A (2012) J Polym Res 19: 9744—each incorporated herein by reference in its entirety].

Ceramic materials have excellent thermal properties and they are being used to enhance the thermal stability of the polymer blends. This enhancement can be observed from the increase in the activation energy of degradation [Shi X, Wang J, Cai X (2013) International Polymer Processing 28: 228-235—incorporated herein by reference in its entirety]. In addition to the size and type of the filler, its shape plays a major role in the properties of the polymer composites. It is found that sphere like geometry of $CaCO_3$ gives the high thermal stability while cubic $CaCO_3$ has an adverse effect on the toughness [Kamil S, Fatih D, Mehmet B, Kaya I (2009) J Macromol Sci Part A 46:949-958—incorporated herein by reference in its entirety]. Similarly, statistical analysis showed that the grade of the same filler is a significant factor in determination of rheological properties of the polymer [Teixeira S C S, Moreira M M, Lima A P, Santos L S, De Rocha B M (2005) De Lima. Polym Test 24:983-987— incorporated herein by reference in its entirety]. Calcium zirconate ($CaZrO_3$) is a ceramic material which has excellent thermal properties like high melting point of 2368° C.

The present disclosure provides methods for producing polyethylene where calcium zirconate is incorporated into the polymer as a filler.

BRIEF SUMMARY OF THE INVENTION

According to a first aspect, the present disclosure relates to a method for producing a high-density polyethylene nanocomposite. The method comprises polymerizing, in a reactor, ethylene in a polymerization mixture comprising a zirconocene catalyst, a methylaluminoxane cocatalyst and a calcium zirconate nanofiller to form the high-density nanocomposite. The calcium zirconate nanofiller is dispersed in a polyethylene matrix.

In one embodiment, the calcium zirconate nanofiller is present, during the polymerizing, in an amount of 0.02-3.0 wt. % per total weight of the high-density polyethylene nanocomposite produced.

In some embodiments, the polymerizing is carried out in a solvent.

In alternative embodiments, the polymerizing is carried out in toluene.

In one embodiment, the zirconocene catalyst has a concentration of 10-30 μmol in the toluene.

In some embodiments, the methylaluminoxane cocatalyst is present, during the polymerizing, at a methylaluminoxane/toluene volume ratio of 1:10-20.

In certain embodiments, the polymerizing is carried at 1.0-1.5 bar.

In certain embodiments, the polymerizing is carried at 25-35° C.

In one embodiment, the reactor is a Schlenk flask comprising a glove box.

In some embodiments, the method for producing the high-density polyethylene nanocomposite further comprises: dissolving the zirconocene catalyst and the calcium zirconate nanofiller in the toluene in the presence of an inert gas in the reactor; removing the inert gas from the reactor and injecting the ethylene into the reactor; and adding the methylaluminoxane cocatalyst into the polymerization mixture.

In one embodiment, the calcium zirconate nanofiller has an average particle size of 30-75 nm.

In one or more embodiments, the calcium zirconate nanofiller increases activity of the zirconocene catalyst by 5-45%.

In one or more embodiments, the calcium zirconate nanofiller converts the polyethylene matrix from a fibrillar morphology to a smooth morphology.

In one or more embodiments, the method produces a high-density polyethylene nanocomposite having 60-80% crystallinity.

In one or more embodiments, the method produces a high-density polyethylene nanocomposite having a molecular weight of 30-80 kDa.

In one or more embodiments, the method produces a high-density polyethylene nanocomposite having a heat release rate of 1200-1300 W/g.

In one or more embodiments, the method produces a high-density polyethylene nanocomposite having a decomposition temperature of 500-525° C.

In one or more embodiments, the method produces a high-density polyethylene nanocomposite that is non-flammable.

In one or more embodiments, the method produces a high-density polyethylene nanocomposite having a polydispersity index of 2.0-3.0.

According to a second aspect, the present disclosure relates to a high-density polyethylene nanocomposite produced by the method in accordance with the first aspect.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Referring now to the drawings, wherein like reference numerals designate identical or corresponding parts throughout the several views.

To prepare a high density polyethylene (HDPE) nanocomposite in accordance with the present disclosure, ethylene gas is polymerized in situ in the presence a zirconocene catalyst ($Cp_2ZrCl_2$), a methylaluminoxane cocatalyst (MAO), a calcium zirconate nanofiller ($CaZrO_3$) and a non-reactive solvent such as but not limited to organic solvents and ionic liquids. and. Examples of non-reactive organic solvents include but are not limited to silsequioxane, $C_5$ or higher paraffins, and aromatic solvents such as toluene, benzene, ethylbenzene, xylene isomer mixture, BTX fraction (mixture of benzene, toluene and xylene isomers), solvent naptha. In one embodiment, toluene is used as the solvent. The ionic liquids may contain water and one or more of cation and anion species selected from ammonium, phosphonium, pyridinium, imidazolium, chloride, bromide, tetrafluoroborate, hexafluorophosphate, trifluoromethanesulfonate, dicyanonitride, bis[((trifluoromethyl)peroxy)sulfane] nitride.

Prior to the polymerization, the catalyst powder and the nanofiller powder are added to and/or mixed with toluene in a reactor in the presence of an inert gas (e.g. nitrogen or argon). At least the nanofiller powder remains suspended in the toluene solvent without being dissolved. The reactor is preferably a Schlenk flask having a glove box and a magnetic stirrer, but is not so limited. Commercially available industrial olefin polymerization reactors having a fixed bed or a fluidized bed can also be used to carry out the ethylene polymerization in accordance with the present disclosure, such as but not limited to Pfaudler Glasteel reactors, Polymer Reactor Technology (PRT) multipurpose stainless steel batch reactors and polyethylene reactors manufactured by engineered Pressure Systems, Inc. The catalyst powder and the nanofiller powder can be mixed with the toluene in a glove box, and the polymerization mixture is stirred to mix well. The catalyst powder is added to a final concentration in the polymerization mixture of 10-30 μmol, preferably 15-25 μmol, more preferably 18-22 μmol. The amount of the calcium zirconate nanofiller powder present in the polymerization mixture is 0.02-5.0 wt % (per total weight of the HDPE nanocomposite produced), preferably 0.05-3.0 wt. %, preferably 0.05-1.0 wt. %, more preferably 0.1-0.8 wt. %. The resulting HDPE nanocomposite contains the same amount of calcium zirconate nanofiller. Relative to the zirconocene catalyst, the amount of the calcium zirconate nanofiller powder is 250-750 wt. % per zirconocene catalyst weight, preferably 300-600 wt. %, more preferably 350-550 wt. %. In one embodiment, the amount of the zirconocene catalyst present in the polymerization mixture is 6 mg while the amount of the calcium zirconate nanofiller is 15 mg. In another embodiment, the polymerization mixture contains 6 mg of the zirconocene catalyst and 30 mg of the calcium zirconate nanofiller. In yet another embodiment, the polymerization mixture contains 6 mg of the zirconocene catalyst and 45 mg of the filler.

After the polymerization mixture is prepared, the inert gas filling the reactor is optionally removed, for example, by vacuum, and the reactor is injected with ethylene gas until a saturation point is reached. The MAO cocatalyst is then added into or mixed with the reactor and slurry polymerization of ethylene is initiated. In one embodiment, the MAO cocatalyst is in solution form (10-20 wt. % in toluene) and the MAO cocatalyst is added at a MAO/toluene solvent ratio of 1:10-20, preferably 1:12-20, more preferably 1:15-18. The temperature is maintained at 25-40° C. throughout the preparation of the polymerization mixture and ethylene polymerization step, preferably 25-35° C., more preferably 28-32° C. The pressure is kept at near atmospheric pressure at 1.0-1.5 bar, preferably 1.1-1.4 bar, more preferably 1.2-1.3 bar.

The ethylene is polymerized for 10 min to 2 h, preferably 10 min to 1 h, more preferably 15 min to 45 min, for example, 25 min to 35 min. The polymerization reaction can be quenched with acidified methanol (5 vol. % HCl) and the HDPE nanocomposite product can be washed with excess amount of methanol and dried at 45-60° C., preferably 45-55° C. for 4-10 h.

In an alternative embodiment, the HDPE nanocomposite may be synthesized by gas phase polymerization of ethylene, such as the UNIPOL™ polyethylene process in a single, low-pressure, gas-phase reactor. The gas-phase polymerization is carried out in the presence of a catalyst mixture containing the zirconocene catalyst, the methylaluminoxane cocatalyst and the calcium zirconate nanofiller.

In the polymerization described herein, calcium zirconate nanopowder is used as a doping agent or filler that is dispersed directly through the HDPE matrix during polymerization. Calcium zirconate is preferably not used as a carrier or support material for the catalyst. The calcium zirconate nanopowder used in the method has an average particle size of 25-100 nm, preferably 30-75 nm, more preferably 40-60 nm. Nanoparticle reinforcement with calcium zirconate nanopowder can substantially improve HDPE properties such as mechanical strength, molecular weight, molecular distribution, gas barrier properties, polymer crystallinity and flame retardancy. For example, the molecular weight of the HDPE nanocomposite can be increased by 20-30%, preferably 22-28%, more preferably 23-25%. The polymer crystallinity can be increased by 2-10%, preferably 3-8%, more preferably 5-7%. The flame retardency of the HDPE nanocomposite can be improved, as indicated by a reduction in heat release rate, by 2-10%, preferably 5-10%, more preferably 8-10%.

Additionally, the presence of the calcium zirconate nanofiller may function to enhance the polymerization reaction, for example, by increasing activity of the zirconocene catalyst. The zirconocene catalyst activity can be increased by at least 5% (relative to the same reaction without the calcium zirconate nanofiller), preferably 5-45%, more preferably 15-45%. The activity of the zirconocene catalyst in the ethylene polymerization is $50\text{-}500 \times 10^{-3}$ gPE/mol h bar, preferably $100\text{-}250 \times 10^{-3}$ gPE/mol h bar, preferably $130\text{-}190 \times 10^{-3}$ gPE/mol h bar, preferably $150\text{-}190 \times 10^{-3}$ gPE/mol h bar, more preferably $165\text{-}190 \times 10^{-3}$ gPE/mol h bar.

The HDPE nanocomposites have a polymer crystallinity (percentage crystallinity), as determined by differential scanning calorimetry (DSC) or X-ray diffraction analysis (XRD), of 60-100%, preferably 60-80%, more preferably 65-75%. The crystallization peak temperature, as determined by crystallization analysis fraction (CRYSTAF), lies within the range of 70-100° C., preferably 75-95° C., preferably 80-90° C., preferably 80-85° C., more preferably 82-84° C.

The molecular weight of the HDPE nanocomposites described herein and produced with the methods described herein, as determined by gel permeation chromatography, is 10-1,000 kDa, preferably 20-500 kDa, more preferably 25-100 kDa, more preferably 30-80 kDa, more preferably 50-70 kDa. The incorporation of the calcium zirconate nanofiller during polymerization of ethylene is found to increase the produced HDPE nanocomposite molecular weight by 20-30% in certain embodiments Further, methods provided herein produce HDPE nanocomposites having polydispersity index (PDI) values within the range of 1.5-3.0, preferably 2.0-3.0, more preferably 2.5-3.0. The incorporation of calcium zirconate during ethylene polymerization is also found to enhance the molecular weight distribution of the produced HDPE nanocomposites in some embodiments, as reflected by the PDI values.

As determined by fire testing technique (FTT) microcalorimetry, the HDPE nanocomposites have a heat release rate of 1000-1500 W/g, preferably 1100-1400 W/g, preferably 1200-1300 W/g, preferably 1220-1270 W/g, more preferably 1230-1260 W/g. The incorporation of calcium is found to increase flame retardency of HDPE, as reflected in by a reduction in the heat release rates in the HDPE nanocomposites. In some embodiments, the HDPE produced by the method of the present disclosure is non-flammable.

The decomposition temperature of the HDPE nanocomposites, also determined by FTT microcalorimetry, is 500-550° C., preferably 500-525° C., more preferably 510-520° C.

The melting temperature of the HDPE nanocomposites is at least 130° C., preferably 130-140° C., preferably 130-135° C. In certain embodiments, the HDPE nanocomposite melting temperature can be increased by 0.1-0.5% (relative to neat HDPE).

Methods described herein produce HDPE nanocomposites having a smooth morphology, as observed microscopically with scanning electron microscopy, transmission electron microscopy or a combination thereof. The presence of the calcium zirconate nanofiller, which is dispersed across the PE matrix, converts the fibrillar morphology of the PE matrix into a smooth morphology.

EXAMPLES

In the following examples, polymerization of ethylene was carried out to form polyethylene nanocomposites with calcium zirconate nanopowder. The polyethylene nanocomposites having 0.6 wt. % of nanofillers where the nanofillers were present during polymerization was found to lead to the highest catalyst and cocatalyst activity. The molecular weight of the polyethylene nanocomposite was found to be the highest 0.6 wt. % of calcium zirconate nanofillers. Differential scanning calorimetry (DSC) and wide angle X-ray diffraction (WAXD) show that at 0.6 wt. % of calcium zirconate nanofillers, the percentage crystallinity is slightly increased. CRYSTAF analysis also shows that there is an increase in the crystallinity by adding the nanofiller. It is also apparent from the microcalorimeter data that, when increasing the nanofiller concentration there is decrease in heat release rate which indicates the increase in flame retardency. The fibril morphology of the polyethylene fracture surface changed to a smoother one with the incorporation of calcium zirconate nanofiller. The following examples are included herein for illustrative purposes, and are not intended to limit to scope of the appended claims.

Example 1

Materials

All reactions were carried out under nitrogen by using standard Schlenk and glove box techniques. Calcium zirconate nanopowder having size less than 50 nm, zirconocene (catalyst), and MAO (co-catalyst) were purchased from Sigma Aldrich and used without further purification. Solvents were purified by standard solvent extraction techniques. Nitrogen and ethylene monomer (99.95% purity) were purchased from SIGAS (Saudi Industrial Gas Company).

Example 2

Ethylene Polymerization

Polymerization of ethylene was carried out in 250 ml Schlenk flask equipped with a magnetic stirrer. The solvent (80 ml of toluene), catalyst and required amount of calcium zirconate were added to the reactor inside the glove box. The reactor was then taken outside the glove box and placed in a previously settled constant temperature bath (30° C.). Ethylene gas was introduced into the reactor after evacuating the nitrogen gas by applying vacuum. When no more absorption of ethylene was observed, cocatalyst (MAO) was injected into the reactor using gaseous syringe. The pressure of the reactor was maintained at 1.3 bar immediately after the addition of cocatalyst. The polymerization was quenched after the desired time (0.5 h) by the addition of methanol containing 5 vol. % of HCl after the unreacted monomer was vented. The polymer was washed with excess amount of methanol and dried at 50° C. in vacuum oven for 6 h.

Figure 1:
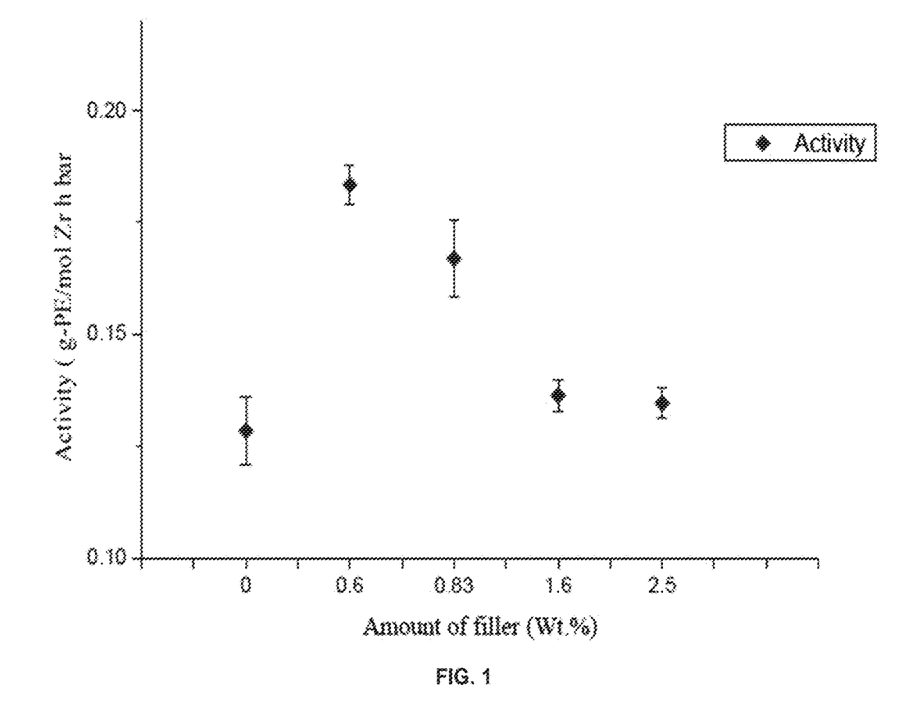
FIG. 1 is a plot showing activity of polymer nanocomposites with different amounts of filler.

Table 1 summarizes the results of polymerization activity and polymer characteristics. The activity of polymerization was found to increase with increase in filler concentration and the maximum activity was obtained at 0.6 wt. % of filler content (Entry 2, Table 1). However, further increase in the filler concentration reduces the polymerization activity as shown in entries 3 and 4 in Table 1. At higher concentrations of the filler, the polymerization activity reduced because the high amount of the filler leads to some agglomeration, which deactivates or hinders the active site of the catalyst. Previous studies have shown that different fillers led to higher activity and/or higher molecular weight [Abdul Kaleel S H, Bahuleyan B K, De S K, Khan M J, Sougrat R, Al-Harthi M A (2012) J Ind and Eng Chem 18:1836-1840; Bahuleyan B K, Atieh M A, De S K, Khan M J, Al-Harthi M A (2012) J Polym Res 19:9744—each incorporated herein by reference in its entirety]. FIG. 1 reveals the effect of filler concentration on the activity of the catalyst.

Example 3

Differential Scanning Calorimetry (DSC)

The crystallization and melting behavior of PE-nano composite samples were determined by DSC-Q1000, TA instruments, USA. High purity nitrogen was purged through the calorimeter. The samples were heated from room temperature to 160° C. at 10° C./min heating rate and cooled to room temperature at the same rate under nitrogen environment. Second (cooling scan) and third cycles (second heating scan) were taken to determine crystallization and melting temperatures respectively.

Figure 2:
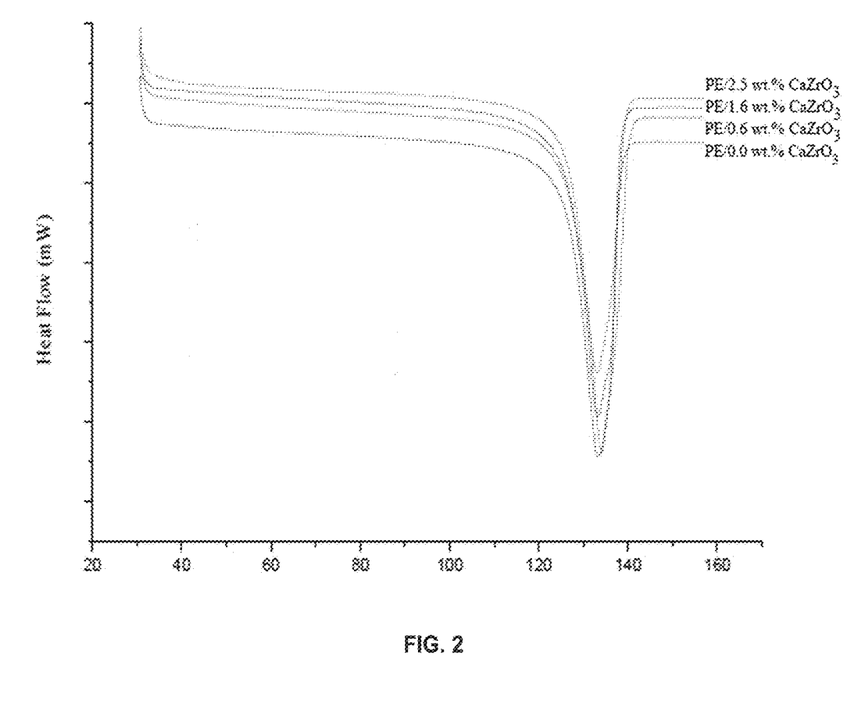
FIG. 2 shows DSC heating curves of nano-$CaZrO_3$-filled PE composites.
Figure 3A:
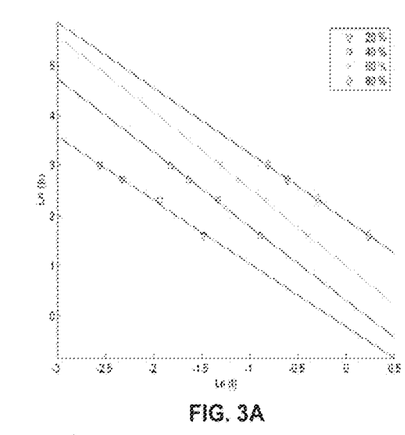
FIG. 3A is a mean ordinate (MO) method plot for a neat PE.
Figure 3B:
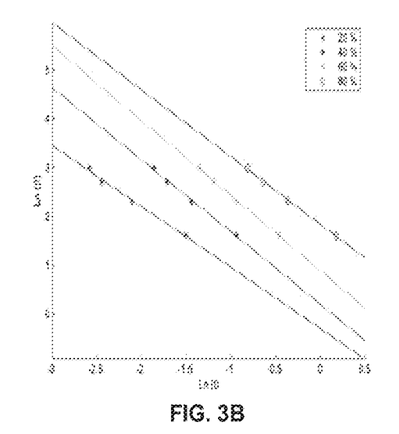
FIG. 3B is a MO method plot for PE/0.6 wt. % $CaZrO_3$.
Figure 3C:
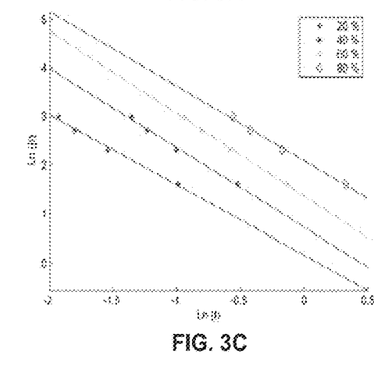
FIG. 3C is a MO method plot for PE/1.6 wt. % $CaZrO_3$.
Figure 3D:
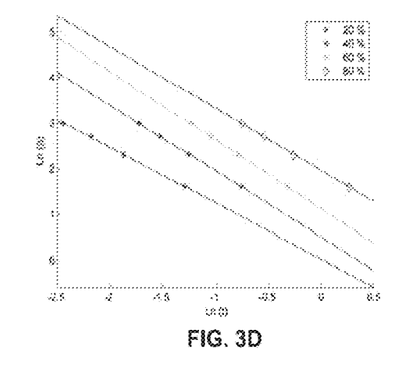
FIG. 3D is a MO method plot for PE/2.5 wt. % $CaZrO_3$.

The effect of nanocalcium zirconate on the melting temperature ($T_m$) and percentage crystallinity ($X_c$) of polyethylene is determined by DSC measurements. FIG. 2 shows the heating curve of the polymer nanocomposites and the melting temperature ($T_m$). Percent crystallinity ($X_c$) and heat of fusion ($\Delta H$) were given in Table 1. From both FIG. 2 and Table 1, it can be seen that there is only marginal difference in the $T_m$. In case of $X_c$, there is 4% increase by adding the 0.6 wt. % of nanofiller and further incorporation shows the decreasing trend. This increase when adding small percentage of the nanofiller is attributed to the heterogeneous crystallization on its surface (nanofillers acting as nucleating agents), which leads to the increase in the crystallinity of the composites [Hoffman D M, McKinley B M (1985) Poly Eng and Sci 25:562-569; Bahuleyan B K, De S K, Sarath P U, Furquan S A, Khan J K, Emwas A H, Al-Harthi M A (2012) J Macromolecular Research 20:772-775—each incorporated herein by reference in its entirety]. At higher loading of nanofiller, agglomeration of filler particles may occur and mobility of polymer chains becomes reduced with consequent decrease in the size of crystallite and hence a reduction in the percent crystallinity is observed [Gu J, Zhang Q, Dang J, Zhang J, Yang Z (2009) Poly Eng and Sci 49: 1030-1034; Abdul Kaleel S H, Bahuleyan B K, De S K, Khan M J, Al-Harthi M A (2011) J Nan Mat—each incorporated herein by reference in its entirety].

The non-isothermal crystallization of the nanocomposites was studied using the method proposed by Liu et al. [Liu T, Mo Z, Zhang H (1998) J Appl Poly Sci 67:815-821—incorporated herein by reference in its entirety]. This method is based on the combination of Avrami and Ozawa models [Avrami J (1978) Polymer 19:1142-1144; Ozawa T (1971) Polymer 12:150-158—each incorporated herein by reference in its entirety]. This equation is given below:

$$Ln[\beta]=Ln[F(T)]-aLn[t] \quad \text{(Eq. 1)}$$

TABLE 1

Ethylene polymerization results at 1.3 bar[a]

| Entry No. | Filler (wt. %) | Activity[c] | $T_m$[d] (° C.) | $\Delta H$[d] (J/g) | $X_c$[d] (%) | $M_w$[e] (×10[3]) | PDI[e] | $X_c$[f] (%) |
|---|---|---|---|---|---|---|---|---|
| 1. | 0.00 | 128.0 ± 0.01 | 133.7 ± 0.40 | 202.3 ± 0.30 | 69.5 ± 0.10 | 52.2 ± 0.80 | 2.6 ± 0.10 | 67.6 ± 0.10 |
| 2. | 0.60 | 183.4 ± 0.00 | 134.0 ± 0.20 | 216.2 ± 0.50 | 73.8 ± 1.00 | 63.2 ± 2.50 | 2.8 ± 0.10 | 71.0 ± 0.10 |
| 3. | 1.60 | 136.3 ± 0.00 | 133.1 ± 0.10 | 202.7 ± 2.00 | 69.7 ± 1.00 | 66.8 ± 0.05 | 1.8 ± 0.04 | 67.3 ± 0.15 |
| 4. | 2.50 | 134.6 ± 0.00 | 132.3 ± 0.10 | 200.4 ± 2.00 | 68.0 ± 1.00 | 32.5 ± 0.10 | 2.5 ± 0.10 | 67.2 ± 0.10 |

[a]Polymerization conditions: solvent toluene = 80 mL, cocatalyst MAO = 5 mL, temp = 30° C. Cp$_2$ZrCl$_2$ catalyst amount = 20.5 μmol, filler is CaZrO$_3$ nanopowder.
[b]Control
[c]×10$^{-3}$ gPE/mol h bar
[d]Determined by DSC measurements
[e]Determined by GPC analysis
[f]Determined by XRD analysis In Eq. 1, $F(T)=[K(T)/k_t]^{1/m}$ and a=n/m which stands for the ratio of Avrami exponent to the Ozawa exponent. F(T) indicates the degrees of cooling required in a unit time for a specific degree of relative crystallinity. The smaller the value of F(T), the easier the crystallization will be. For this method to successfully describe the crystallization process, the plot of Ln[β] vs Ln[t] should be a straight line.

F(T) and a(T) can be calculated from intercept and slope of the straight line respectively. In order to apply this method for the analysis, DSC tests were conducted at multiple cooling rates. FIGS. 3A-3D show the MO (mean ordinate) plots for neat polyethylene and all the nanocomposites. From these figures, it can be seen that the line graphs are straight lines for all samples. The summarized results from the MO methods are shown in Table 2. It is observed that F(T) for PE/0.6 wt. % $CaZrO_3$ is less than neat PE, which indicates a faster crystallization rate. For all the other nanocomposites, PE/1.6 wt. % $CaZrO_3$ and PE/2.5 wt. % CaZrO3, F(T)) at the given crystallinity is higher as compared to neat Polyethylene. This indicates that a higher amount of the nanofiller restricts the chain movements and makes the crystallization difficult.

TABLE 2

Summarized MO analysis results.

| Sample | X (T) | F (T) | α (T) |
|---|---|---|---|
| PE/0.0 wt. % $CaZrO_3$ | 0.20 | 0.80 | 1.27 |
| | 0.40 | 1.35 | 1.48 |
| | 0.60 | 2.71 | 1.53 |
| | 0.80 | 6.79 | 1.32 |
| PE/0.6 wt. % $CaZrO_3$ | 0.20 | 0.74 | 1.25 |
| | 0.40 | 1.22 | 1.48 |
| | 0.60 | 2.44 | 1.53 |
| | 0.80 | 6.30 | 1.38 |
| PE/1.6 wt. % $CaZrO_3$ | 0.20 | 0.77 | 1.57 |
| | 0.40 | 1.37 | 1.88 |
| | 0.60 | 3.16 | 1.88 |
| | 0.80 | 7.50 | 1.62 |
| PE/2.5 wt. % $CaZrO_3$ | 0.20 | 1.02 | 1.22 |
| | 0.40 | 1.66 | 1.44 |
| | 0.60 | 3.08 | 1.50 |
| | 0.80 | 7.12 | 1.35 |

Example 4

Gel Permeation Chromatography (GPC)

The molecular weight and molecular weight distribution were determined by gel permeation chromatography (Viscotek HTGPC 130A model, 140° C.) using 1,2,4-trichlorobenzene as a carrier solvent.

The results of Gel Permeation Chromatography (GPC) in Table 4 support the higher melting temperature in PE/0.6 wt. % CaZrO3 nanocomposites. The Molecular weights (Mw) of the nanocomposites are given in the Table 1. Polyethylene with 0.6 wt. % of nanofiller composites shows higher Mw as compared to the control (neat PE).

Example 5

Crystallization Analysis Fractionation (CRYSTAF)

Crystallization analysis was determined by CRYSTAF (Polymer Char, Spain). Crystallization was carried out by using 1,2,4 trichlorobenzene in stainless steel stirred vessel of 50 mL volume. Crystallization rate of 0.2° C./min was used for the analysis. The IR cell was kept heated isothermally during the whole experiment at a temperature of 150° C.

Figure 4:
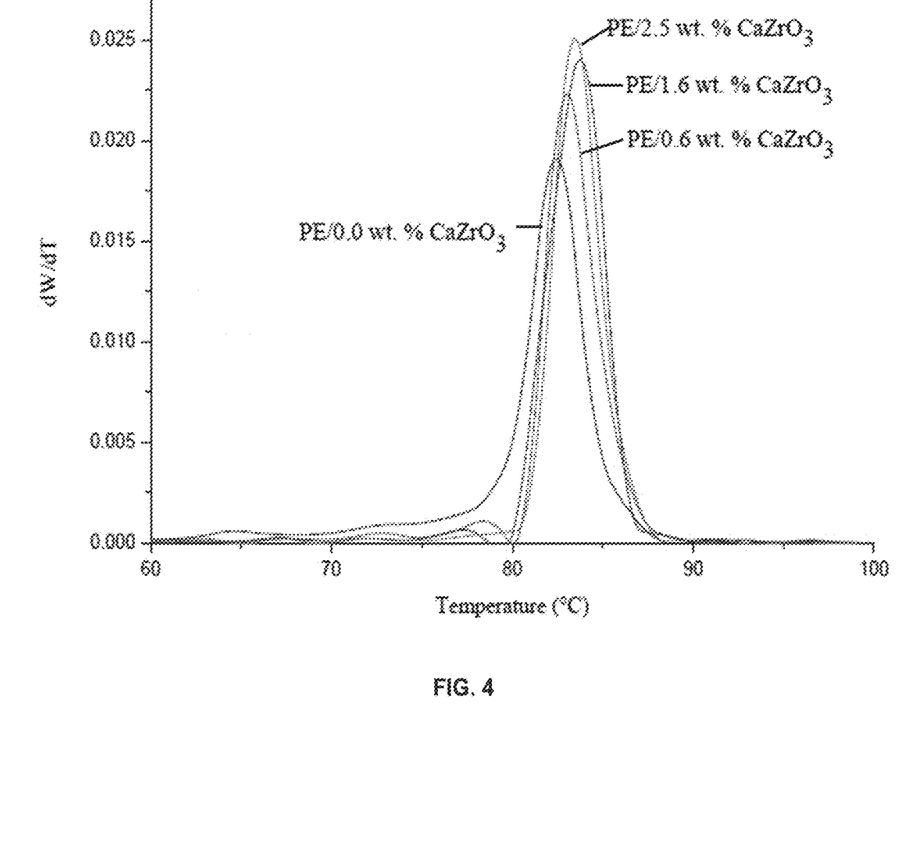
FIG. 4 shows CRYSTAF analyses curves of PE nanocomposites using $Cp_2ZrCl_2$ catalyst at different amounts of $CaZrO_3$ nanofiller with neat PE.

The Chemical Composition Distribution (CCD) was found by using the CRYSTAF analysis based on the continuous crystallization of polymer chains from a dilute solution [Soares, J B P, Anantawaraskul S (2005) J Poly Sci Part B—Poly Phy 43: 1557-157—incorporated herein by reference in its entirety]. This technique is based on the fact that semi crystalline polymers in solution at higher temperature will crystallize and precipitate as the solution temperature is lowered [Nieto J, Oswald T, Blanco F, Soares J B P, Monrabal B (2001) J Poly Sci Part B—Poly Phy 39:1616-1628—incorporated herein by reference in its entirety]. The CRYSTAF results for PE nanocomposites with different concentrations of the calcium zirconate nanofiller are presented in FIG. 4. From FIG. 4 and from Table 3, it can be inferred that the crystallization peak temperatures lies between 82° C. and 84° C. for both control (Entry 1, Table 3) and polyethylene nanocomposites. As shown in FIG. 4, there is a slight shifting of the curves from low temperature to higher temperature indicating that there is increasing tendency of crystallinity of the polyethylene nanocomposites by adding nanofiller. These results are matched with crystallinity results obtained from DSC analysis (Table 1).

TABLE 3

CRYSTAF analysis results for PE nanocomposites.

| Entry No. | Filler (wt. %) | $T_c$ (° C.)[a] | $T_w$[b] | $T_n$[c] |
|---|---|---|---|---|
| 1 | 0.00 | 82.7 ± 0.2 | 79.9 ± 1.3 | 77.4 ± 1.8 |
| 2 | 0.60 | 82.8 ± 0.2 | 83.3 ± 1.5 | 85.0 ± 4.6 |
| 3 | 1.60 | 83.0 ± 0.7 | 82.1 ± 1.0 | 81.5 ± 1.6 |
| 4 | 2.50 | 83.5 ± 0.0 | 82.5 ± 0.6 | 82.5 ± 0.6 |

[a] CRYSTAF peak temperature or crystallization temperature.

[b] weight average crystallization temperature calculated according to $T_w = (\Sigma C_i T_i)/C_i$, where $C_i$ is the concentration of the polymer in solution at the $i^{th}$ data point and $T_i$ is the temperature at the $i^{th}$ data point.

[c] number average crystallization temperature according to $T_n = \Sigma C_i/(\Sigma(C_i T_i))$.

Example 6

Microcalorimetry

Figure 5:
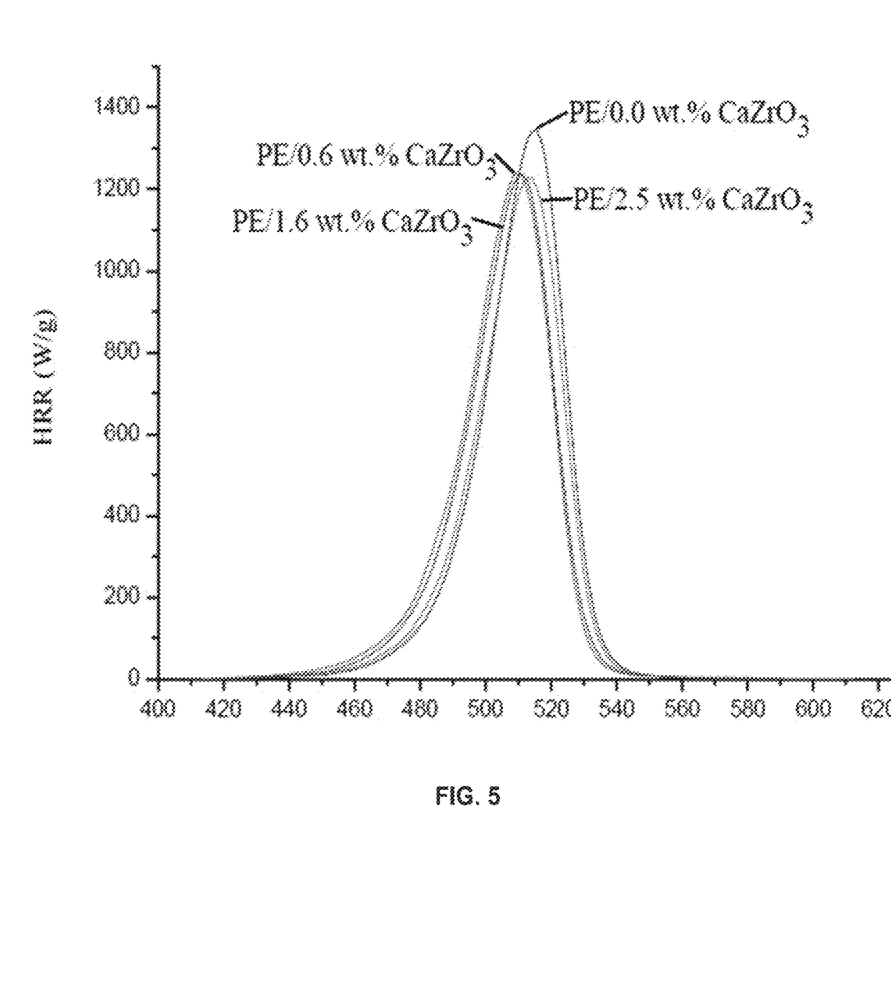
FIG. 5 shows the microcalorimeter results (heat release rate vs. temperature) of PE with different concentrations of $CaZrO_3$ nanopowder.

A combustibility study of the PE nano composites was conducted using a microcalorimeter, in terms of heat release rate (HRR) and decomposition/ignition temperature. Both heat release rate and ignition temperature of the samples were determined by using fire testing techniques (FTT microcalorimeter). Decomposition temperatures are shown in FIG. 5 and Table 4. FIG. 5 shows the effect of nanofiller on heat release rate of the polymer nanocomposites. It can be seen that on adding the nanofiller, the HRR starts to lower, which indicates an increase in the flame retardency [Pal G, Mackasy H (1991) Plastics Their Behaviour in Fires. Acta Polymerica, Akademie Verlag GmbH, Berlin, Germany; Troitzsch J (1990) International Plastics Flammability Handbook, Hanser, 2nd edition—each incorporated herein by reference in its entirety].

TABLE 4

Microcalorimetry results showing decomposition temperature (° C.) and heat release rate (W/g)

| Material | Decomposition temperature (° C.) | HRR (W/g) |
|---|---|---|
| PE/0.00 wt. % CaZrO$_3$ | 514.5 ± 0.3 | 1361.0 ± 17.0 |
| PE/0.60 wt. % CaZrO$_3$ | 511.5 ± 0.4 | 1237.0 ± 0.01 |
| PE/1.60 wt. % CaZrO$_3$ | 512.7 ± 0.8 | 1260.0 ± 23.0 |
| PE/2.50 wt. % CaZrO$_3$ | 513.9 ± 0.4 | 1239.0 ± 11.2 |

Example 7

Scanning Electronic Microscopy (SEM)

Figure 6A:
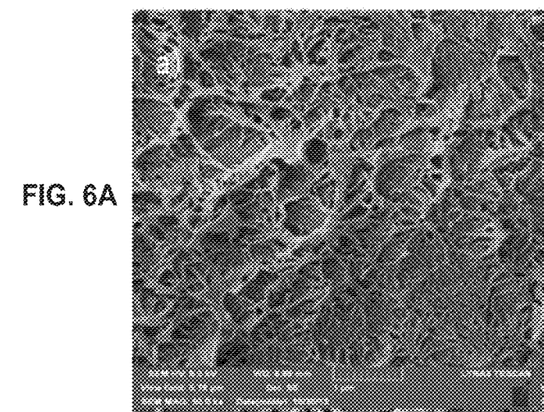
FIG. 6A is an SEM image of a neat PE nanocomposite (control).
Figure 6B:
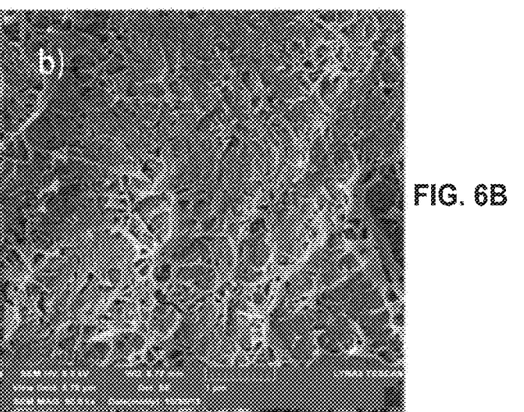
FIG. 6B is an SEM image of PE/0.6 wt. % $CaZrO_3$.
Figure 6C:
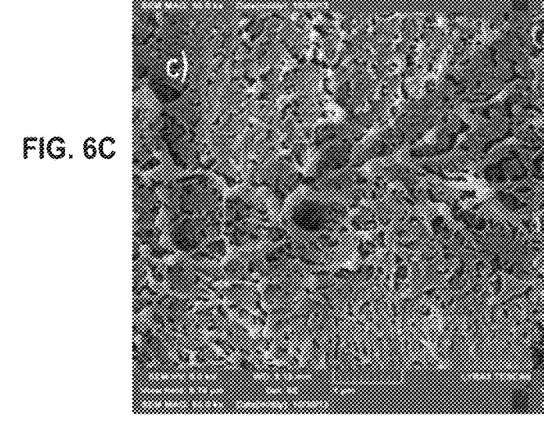
FIG. 6C is an SEM image of PE/1.6 wt. % $CaZrO_3$.
Figure 6D:
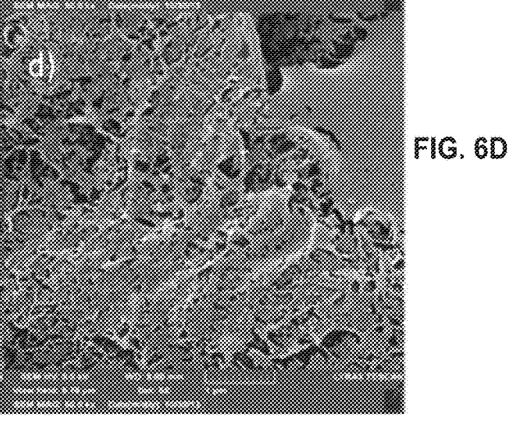
FIG. 6D is an SEM image of PE/2.5 wt. % $CaZrO_3$.

Surface morphology of the neat PE and its nanocomposites of the present disclosure were studied using by Scanning Electron Microscopy (SEM) analysis. The SEM images were recorded using JSM-6460LV (Jeol) at magnification from 500× to 2500× with a resolution of 3.5 nm and a voltage of 15 kV. The SEM micrograph of FIG. 6A, of the fractured surface of synthesized neat polyethylene shows a fibrils-type morphology. In FIGS. 6B-6D, it can be seen that the fibril density progressively diminished due to an increasing presence of the calcium zirconate nanofiller being embedded into the PE matrix. In other words, the nanofiller could act as a bridge between the fibrils and convert the PE nanocomposite to a smoother morphology.

Example 8

X-Ray Diffraction Analysis (XRD)

Figure 7:
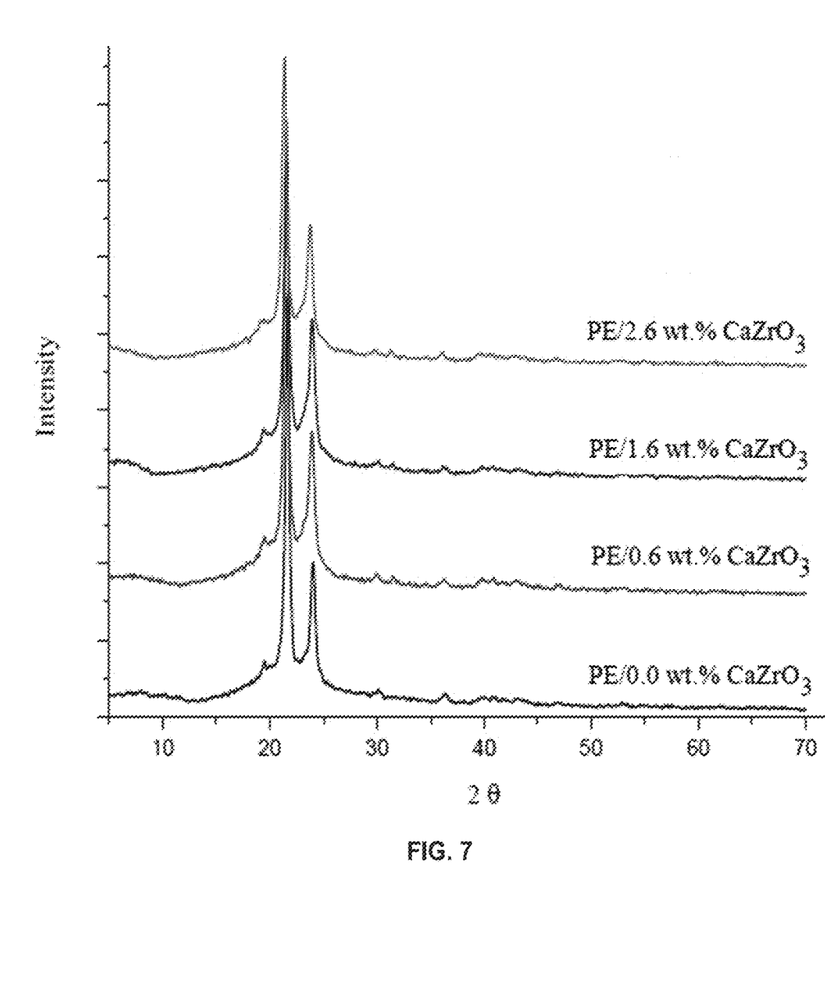
FIG. 7 shows the XRD analysis results of PE nanocomposites at different concentrations of $CaZrO_3$ nanofiller with neat PE.

Wide angle X-ray diffraction (WAXD) was used to find out the crystallinity of the neat PE and PE nanocomposites. The crystallinity was determined by XRD D8 advance X-ray instrument with wavelength of λ=1.542 A° and 2 θ range from 5°-70°. Comparison of WAXD pattern of polyethylene and its nanocomposites are shown in FIG. 7. From WAXD, the percentage crystallinity can be calculated using a previously reported method [Sreekumar P A, Al-Harthi M A, De S K (2012) J Comp Mat 46:3181-3187—incorporated herein by reference in its entirety]. Table 1 presents the percentage of the crystallinity, which is calculated by both WAXD and DSC where similar trends can be observed in both techniques, i.e. a slight increase in crystallinity at 0.6 wt. % CaZrO$_3$ nanofiller.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. A method for producing a high-density polyethylene nanocomposite, comprising:
   mixing a zirconocene catalyst and a calcium zirconate nanofiller in a solvent in a reactor;
   injecting ethylene into the reactor; followed by
   adding a methylaluminoxane cocatalyst into the reactor thereby polymerizing ethylene and forming the high-density polyethylene nanocomposite;
   wherein the calcium zirconate nanofiller is dispersed in a polyethylene matrix, and the calcium zirconate nanofiller is not a support material for the zirconocene catalyst.

2. The method of claim 1, wherein the calcium zirconate nanofiller is present in an amount of from 0.02 to 3.0 wt. % per total weight of the high-density polyethylene nanocomposite produced.

3. The method of claim 1, wherein the solvent is toluene.

4. The method of claim 3, wherein the zirconocene catalyst has a concentration of from 10 to 30 μmol in toluene.

5. The method of claim 3, wherein the methylaluminoxane cocatalyst is present at a methylaluminoxane/toluene volume ratio of from 1:10 to 1:20.

6. The method of claim 1, wherein the polymerizing is carried out at a pressure of from 1.0 to 1.5 bar.

7. The method of claim 1, wherein the polymerizing is carried out at a temperature of from 25 to 35° C.

8. The method of claim 1, wherein the reactor is a Schlenk flask in a glove box.

9. The method of claim 1, wherein the calcium zirconate nanofiller results in the polyethylene matrix having a smooth morphology.

10. The method of claim 1, producing a high-density polyethylene nanocomposite having 60 to 80% crystallinity.

11. The method of claim 1, producing a high-density polyethylene nanocomposite having a molecular weight of from 30 to 80 kDa.

12. The method of claim 1, producing a high-density polyethylene nanocomposite having a heat release rate of from 1200 to 1300 W/g.

13. The method of claim 1, producing a high-density polyethylene nanocomposite having a decomposition temperature of from 500 to 525° C.

14. The method of claim 1, producing a high-density polyethylene nanocomposite that is non-flammable.

15. The method of claim 1, producing a high-density polyethylene nanocomposite having a polydispersity index of from 2.0 to 3.0.

16. The method of claim 1, wherein the calcium zirconate nanofiller increases an activity of the zirconocene catalyst by at least 5%.

17. The method of claim 16, wherein the calcium zirconate nanofiller increases the activity of the zirconocene catalyst by 5 to 45%.

18. The method of claim 1, wherein the calcium zirconate nanofiller has an average particle size of from 25 to 100 nm.

19. The method of claim 18, wherein the average particle size of the calcium zirconate nanofiller is from 30 to 75 nm.

20. The method of claim 1, wherein the polymerizing is carried out for a duration of from 10 minutes to 2 hours.

* * * * *